United States Patent [19]
Broeker et al.

[11] Patent Number: 5,453,538
[45] Date of Patent: Sep. 26, 1995

[54] PROCESS FOR THE MANUFACTURE OF AROMATIC DICARBOXYLIC ACIDS UTILIZING CERIUM TO FACILITATE A LOW BROMINE TO METALS CATALYST RATIO

[75] Inventors: Jeffrey L. Broeker; Walter Partenheimer, both of Naperville; Bruce I. Rosen, Morton Grove, all of Ill.

[73] Assignee: Amoco Corporation, Chicago, Ill.

[21] Appl. No.: 195,274

[22] Filed: Feb. 14, 1994

[51] Int. Cl.$^6$ .......................... C07C 51/265; B01J 31/00
[52] U.S. Cl. .......................... 562/409; 562/416; 562/417; 562/480; 562/488; 502/170; 502/171; 502/227; 502/228
[58] Field of Search .................... 562/409, 416, 562/417, 480, 488

[56] References Cited

U.S. PATENT DOCUMENTS

| | | | |
|---|---|---|---|
| 3,683,018 | 8/1972 | Longland | 562/415 |
| 3,845,117 | 10/1974 | Kollar | 562/416 |
| 4,211,882 | 7/1980 | Komatsu et al. | 562/416 |
| 4,312,778 | 1/1982 | Harper | 562/416 |
| 4,346,232 | 8/1982 | Komatsu et al. | 562/416 |
| 4,447,646 | 5/1984 | Johnson et al. | 562/487 |
| 4,835,308 | 5/1989 | Sakakibara et al. | 562/413 |
| 5,081,290 | 1/1992 | Partenheimer et al. | 562/416 |
| 5,118,838 | 6/1992 | Zeitlin et al. | 562/414 |

OTHER PUBLICATIONS

Chemical Abstracts abstract for Japan patent JP 49133347, Dec. 21, 1974, Okushima, et al. inventor (CA82(23):155820j), "Terephthalic Acid".

Chemical Abstracts abstract for publication in Electrooorg. Synth. "Indirect Ectrolysis Involving Phase Transfer Catalysis", Pletcher, author; Edited by Little, R. D., Meeting date 1990, pp. 255–262, Publisher, Dekber, N.Y., 1991. (Ca 116(12):115434a).

API abstract for Japan Patent JP 78020022, assigned to Maruzen Selsiyu Co. Ltd., Mar. 8, 1974, API 74–70143V, "Terephthalic Acid prepared by Oxidation of p-xylene with Oxygen in Presence of Metal Catalysts".

J. Org. Chemistry, vol. 31, No. 6, pp. 2033–2035, Jun. 1966, "Controlled Oxidation of Organic Compounds with Cerium (IV)—2. The Oxidation of Toluene", Trahanovsky, W. S. and Young, L. B.

*Primary Examiner*—Arthur c. Prescott
*Attorney, Agent, or Firm*—Thomas E. Nemo; Wallace L. Oliver

[57] ABSTRACT

A process for the manufacture of aromatic dicarboxylic acids is disclosed using a low bromine to metals ratio facilitated by the use of cerium along with the cobalt and manganese catalyst. Aromatic dicarboxylic acids such as terephthalic acid are useful in the manufacture of fiber, films, bottles and molded products.

14 Claims, 5 Drawing Sheets

PROCESS FOR THE MANUFACTURE OF AROMATIC DICARBOXYLIC ACIDS UTILIZING CERIUM TO FACILITATE A LOW BROMINE TO METALS CATALYST RATIO

BACKGROUND

The liquid phase oxidation of para-, meta- and ortho-xylenes to their corresponding benzene dicarboxylic acids in the presence of bromine and a catalyst containing manganese and cobalt components has been disclosed in U.S. Pat. No. 2,833,816 and has been practiced worldwide. Additionally, the liquid phase oxidation of a dimethylnaphthalene feed material to a naphthalenedicarboxylic acid can also be accomplished in the presence of bromine and a catalyst containing manganese and cobalt components. See for example, U.S. Pat. No. 5,103,933. These benzene dicarboxylic acids and naphthalenedicarboxylic acids are useful for preparing polyester materials. Such polyesters are used to manufacture synthetic fibers and films for textile and packaging applications, respectively.

Although the use of bromine is advantageous for conducting such liquid phase oxidation reactions, its use does have some drawbacks. For example, bromine contributes to the corrosion of the reactor vessel used for the oxidation reaction as well as the equipment used to process the reaction mixture subsequent to the oxidation reaction. The corrosion metals produced thereby contaminate the crude aromatic carboxylic acid product, and these corrosion metals are detrimental to the hydrogenation catalyst used in a subsequent purification step where the aromatic carboxylic acids are treated with hydrogen gas in the presence of the hydrogenation catalyst. Additionally, the bromine in the oxidation reaction mixture contributes to the production of methyl bromide, a gaseous, hazardous compound. Thus, for environmental reasons, it would be desirable to reduce the amounts of methyl bromide produced during the oxidation of a xylene or a dimethylnaphthalene compound to the corresponding aromatic dicarboxylic acid. By reducing the amount of bromine in the oxidation reaction mixture, corrosion is reduced as well as the amount of methyl bromide formed. However, we determined that a reduction in the amount of bromine, i.e. lower molar ratios of bromine to the total amount of cobalt and manganese, causes an unacceptable precipitation of the manganese component of the catalyst. This precipitation is easily identified because it produces a grey colored rather than white aromatic carboxylic acid product. We believe at least part of the manganese precipitates as manganese dioxide.

In commercial scale operation, a major portion of the oxidation catalyst metals are recycled to the oxidation reaction mixture. The catalyst metal recycle is accomplished by separating the oxidation reaction mother liquor from the solid aromatic carboxylic acid product, and part of mother liquor containing dissolved catalyst metals is recycled back to the oxidation reaction mixture. However, the precipitation of the manganese which occurs at low molar ratios of bromine to catalyst metals prevents efficient recycle of the catalyst metals. Additionally, since the precipitation of the manganese occurs in an uneven manner, the mother liquor will have varying levels of catalyst metals making it difficult to recycle the proper amount of catalyst to the oxidation reaction mixture. This results in unacceptable variability in the aromatic carboxylic acid product.

The art, therefore, needs a method to reduce the ratio of bromine to cobalt and manganese catalyst metals used in the liquid phase oxidation of dimethyl aromatic compounds without causing the precipitation of the manganese portion of the catalyst. The instant invention provides such a method.

SUMMARY OF THE INVENTION

We discovered that when cerium is added to the oxidation reaction mixture, the deleterious manganese precipitation is unexpectedly abated, allowing the use of lower ratios of bromine to oxidation catalyst metals.

Thus, we discovered a process for oxidizing dimethyl aromatic compounds with molecular oxygen to aromatic dicarboxylic acids under liquid-phase conditions in the presence of a $C_1$–$C_6$ aliphatic carboxylic acid solvent wherein the aliphatic carboxylic acid is a solvent for the reaction and also for the metal catalysts, at an elevated reaction temperature suitably in the range of about 212° F. to about 486° F., and in the presence of cerium at low molar ratios of bromine to total metals, which process comprises conducting said oxidation in the presence of catalyst system comprising a source of bromine with manganese, cobalt and cerium components, wherein the molar ratio of cerium to cobalt is in the range of about 0.005 to about 1.0 and the molar ratio of bromine to the total of cobalt and manganese is in the range of about 0.1 to less than about 0.5, and wherein cerium functions to prevent the precipitation of manganese. The preferred dimethyl aromatic compounds are para-xylene, meta-xylene, ortho-xylene, and 2,6-dimethyl-naphthalene, which are oxidized by the process of this invention to terephthalic, isophthalic, ortho-phthalic and 2,6-naphthalenedicarboxylic acid, respectively. The most preferred dimethyl aromatic compounds are the dimethyl benzene aromatic compounds, i.e. para-, meta- and ortho-xylene.

DETAILED DESCRIPTION OF THE INVENTION

Our novel process can be conducted either as a batch process or as a continuous process. In either the continuous or batch process, the reactor for the oxidation reaction should be constructed of an inert material. For example, it can be titanium clad. The oxidation reaction temperature is suitably about 212° F. to about 486° F. In the continuous oxidations, a suitable temperature range is about 350° F. to about 450° F., preferably 370° F. to about 400° F. When the continuous oxidation process is conducted in stages, the first stage temperature is suitably about 370° F. to about 400° F., and the second stage temperature is about 340° F. to about 380° F. The source of molecular oxygen for the liquid phase oxidation reactions disclosed herein can vary. For example, the source of molecular oxygen can be air, a mixture of molecular oxygen with air, or a mixture of molecular oxygen with an inert gas such as nitrogen. Pure molecular oxygen can also be used.

The minimum pressure for such oxidations is preferably that pressure which will maintain a substantial liquid phase of dimethyl aromatic compound and about 70 to 80 percent of the reaction solvent. The reaction solvent can suitably be any $C_1$ to $C_6$ fatty acid such as formic acid, acetic acid, propionic acid, n-butyric acid, isobutyric acid, valeric acid, trimethylacetic acid and caproic acid. The preferred solvent is acetic acid or mixtures thereof with water. It is essential that the cerium, manganese, cobalt and bromine be soluble in the $C_1$–$C_6$ fatty acid solvent. The solvent can amount to about one to about ten parts on a weight basis per part of dimethyl aromatic compound such as para-xylene. Suitable reaction gauge pressures for the oxidation reaction are about 0 kg/cm² to about 35 kg/cm², and are typically about 10 kg/cm² to about 30 kg/cm².

This invention is directed to operating a bromine-manganese-cobalt oxidation system for oxidizing dimethyl aromatic compounds at low molar ratios of bromine to cobalt and manganese, but without precipitating out the manganese portion of the catalyst. We discovered that this can suitably be accomplished by adding cerium to the catalyst system. In our liquid phase oxidation process, the mole ratio of manganese to cobalt is about 0.5 to about 10, preferably about 0.7 to about 3.0. To effectively reduce the amount of methyl bromide formed, the molar ratio of bromine to total of cobalt and manganese (i.e. cobalt plus manganese) should be about 0.1 to about 0.45, preferably about 0.125 to about 0.4, more preferably about 0.2 to about 0.40, most preferably about 0.2 to about 0.275. The molar ratio of cerium to cobalt is about 0.005 to about 1.0, preferably about 0.01 to about 0.3, more preferably about 0.05 to about 0.3, and most preferably about 0.1 to about 0.2. When, in the process of this invention for oxidizing a dimethyl aromatic compound to an aromatic dicarboxylic acid, a molar ratio of bromine to total of cobalt and manganese is below about 0.25, or more preferably about 0.15 and below, it is preferable to have the molar ratio of cerium to cobalt be at least about 0.2, more preferably at least about 0.3. That is, at lower molar ratios of bromine to total manganese and cobalt, it is preferable to have greater amounts of cerium in the liquid phase oxidation reaction mixture. The amount of cobalt in the oxidation reaction solvent is suitably about 40 to about 5000 parts per million by weight, more preferably about 100 to about 2000 parts per million by weight. Representative sources of bromine include hydrogen bromide, sodium bromide, elemental bromine, benzyl bromide, tetrabromoethane, and others within the teachings of U.S. Pat. No. 2,833,816. As used herein, the amount of bromine means the amount measured as Br. Thus, the molar ratio of bromine to total of manganese and cobalt is the moles of Br divided by (moles of Mn plus moles of Co). Each of the cobalt and manganese components can be provided in any of their known ionic or combined forms that provide soluble forms of cobalt and manganese in the reaction solvent. For example, cobalt and/or manganese carbonate, acetate, acetate tetrahydrate, and/or bromide can be used. Preferably cobalt and manganese acetate tetrahydrates are used. The preferred bromine source is hydrobromic acid. The cerium source can be any soluble cerium compound and is suitably cerium acetate or other low molecular weight carboxylic acid salts of cerium, such as cerium butyrate or cerium valerate. Cerium bromide, cerium carbonate, cerium formate and like cerium compounds are also suitable.

As discussed hereinabove, aromatic dicarboxylic acids, such as terephthalic acid, produced by the liquid phase, metal catalyzed oxidation of a dimethyl aromatic compound, are generally treated with hydrogen gas in a purification treatment. Suitable methods for such hydrogenation are disclosed in U.S. Pat. Nos. 3,584,039 and 4,892,972, the specifications of which are hereby incorporated by reference, and in U.S. patent application Ser. No. 07/029,037, to Schroeder et al., filed on Mar. 10, 1993.

In the purification process, impure terephthalic acid, for example, is dissolved in water at an elevated temperature, and the resulting solution is hydrogenated, preferably in the presence of a hydrogenation catalyst, e.g., palladium on a carbon support, as described in U.S. Pat. No. 3,726,915 to Pohlmann. This hydrogenation step converts various color bodies and other impurities present in the relatively impure aromatic dicarboxylic acid to colorless products without substantial hydrogenation of the aromatic ring of the aromatic dicarboxylic acid. Another related purification-by-hydrogenation process of aromatic polycarboxylic acids produced by liquid phase catalyst oxidation of polyalkyl aromatic hydrocarbons is described in U.S. Pat. No. 4,405,809 to Stech et al.

The purification step for producing, for example, purified terephthalic acid for use in combination with the process of the present invention is suitably conducted at an elevated temperature and pressure in a fixed catalyst bed. Crude terephthalic acid to be purified is dissolved in water or a like solvent. Although water is a preferred solvent, other suitable solvents include relatively lower molecular weight aliphatic carboxylic acids, alone or admixed with water. Suitable reactor temperatures for use in this purification step are in a range of from about 100° C. to about 350° C. Preferably, temperatures employed in the purification step are in a range of from about 275° C. to about 300° C.

The concentration of aromatic dicarboxylic acid, for example, terephthalic acid, in the solution to be purified by hydrogenation can vary over a relatively wide range. Concentration can be as low as about 5 percent by weight or as high as about 35 percent by weight, based on the weight of the solution. Preferably, the solution concentration of terephthalic acid is in a range of from about 10 to about 30 percent by weight.

Pressure employed in the purification step depends primarily upon the temperature employed therein. Inasmuch as the temperatures at which practical amounts of the impure aromatic dicarboxylic acid may be dissolved in an aforesaid solvent are substantially above the normal boiling point of the solvent, the process pressures are necessarily considerably above atmospheric pressure to maintain the aqueous solution in a liquid phase. In general, the reactor pressure during hydrogenation can be in a range of about 200 to about 1,500 pound per square inch gauge (psig), and usually is in a range of about 900 psig to about 1,200 psig.

In general, the amount hydrogen supplied to the purification reactor under reaction conditions is, of course, sufficient to effect the desired purification by hydrogenation.

As described in U.S. Pat. Nos. 3,584,039; 3,726,915; and 4,405,809, catalysts that are suitable for use in the aforesaid purification step are insoluble under the conditions employed therein and comprise at least one supported or unsupported Group VIII noble metal, whose class includes palladium, rhodium, ruthenium, osmium, iridium, and platinum. Preferably, the noble metal is at least one member of the group consisting of palladium and rhodium. A typical catalyst of palladium on a support comprises from about 0.01 weight percent to about 2 weight percent of palladium, based on total weight of catalyst and calculated as elemental metal. The support or carrier for the palladium is porous and inert, and preferably is active carbon having a surface area of about 600 m2/g to about 1,500 m2/g. Suitable supports for Pd/C hydrogenation catalysts are well-known and are described, inter alia, in U.S. Pat. No. 3,584,039 to Meyer.

Space velocity reported as weight of crude aromatic dicarboxylic acid solution per weight of catalyst per hour in the purification step is in a range of from about 5 hours$^{-1}$ to about 25 hours$^{-1}$, preferably from about 10 hours-1 to about 15 hours-1. Residence time of the solution in the catalyst bed varies, depending upon activity of catalysts present.

A preferred method for hydrogenation of crude 2,6-naphthalene dicarboxylic acid according to the present invention is the subject of U.S. Pat. No. 5,256,817 to Sikkenga and Hoover, the specification of which is incorporated herein by reference. A preferred method for the hydrogenation of isophthalic acid is the subject of U.S. Pat. No. 5,110,984 to Janulis, the specification of which is also incorporated herein by reference.

Corrosion metals produced by high levels of bromine in the hereinabove described liquid phase oxidation of dimethyl aromatic compounds can contaminate the crude aromatic dicarboxylic acid product. When such contaminated product is purified by the hereinabove described hydrogenation reaction, these corrosion metals can deactivate the expensive hydrogenation catalyst. However, by using the instant invention where lower levels of bromine are used, there is less corrosion and less deactivation of the hydrogenation catalyst.

FIGS. 1 through 5 illustrate the advantages of our novel oxidation process. FIGS. 1 through 5 present data for the liquid phase oxidation of para-xylene to terephthalic acid in a two stage reactor using a cobalt-manganese-bromine catalyst system, with and without cerium as noted. At bromine to cobalt plus manganese molar ratios less than or equal to 0.3, the molar ratio of cerium to cobalt was 0.1, when the bromine to cobalt plus manganese was 0.8, the molar ratio of cerium to cobalt was 0.35. In these figures "METALS" refers to the total amount of cobalt and manganese catalyst metals in the reaction mixture; "CAKE" means the terephthalic acid product filter cake formed after separating the product terephthalic acid from the oxidation reaction mother liquor, "MN" means manganese measured by x-ray fluorescence spectroscopy, "PPMW" means parts per million by weight, "L*" is a value of color (grayness) obtained by known procedures such as that described in U.S. Pat. No. 4,892,972, "COX" means total carbon oxides, i.e. carbon dioxide and carbon monoxide, "BR" means bromine, measured as Br, "PX" means para-xylene, "MEBR" means methyl bromide, and "SLURRY OD340" is a color measurement. Slurry OD340 values are obtained by removing a portion of the total reaction mixture from the second stage of a two-stage oxidation reaction, dissolving the slurry in a solution of ammonium hydroxide, removing insolubles by filtration, and measuring the optical density of the filtrate at 340 nanometers. OD340 is discussed in U.S. Pat. No. 4,892,972.

The addition of cerium reduced the manganese on the terephthalic acid to about less than 10 parts per million on a weight basis at a molar ratio of bromine to total of cobalt and manganese of 0.2, and no evidence of cerium precipitation was found. A portion of the precipitated manganese has been identified as being in the $Mn^{+4}$ oxidation state.

Figure 1:
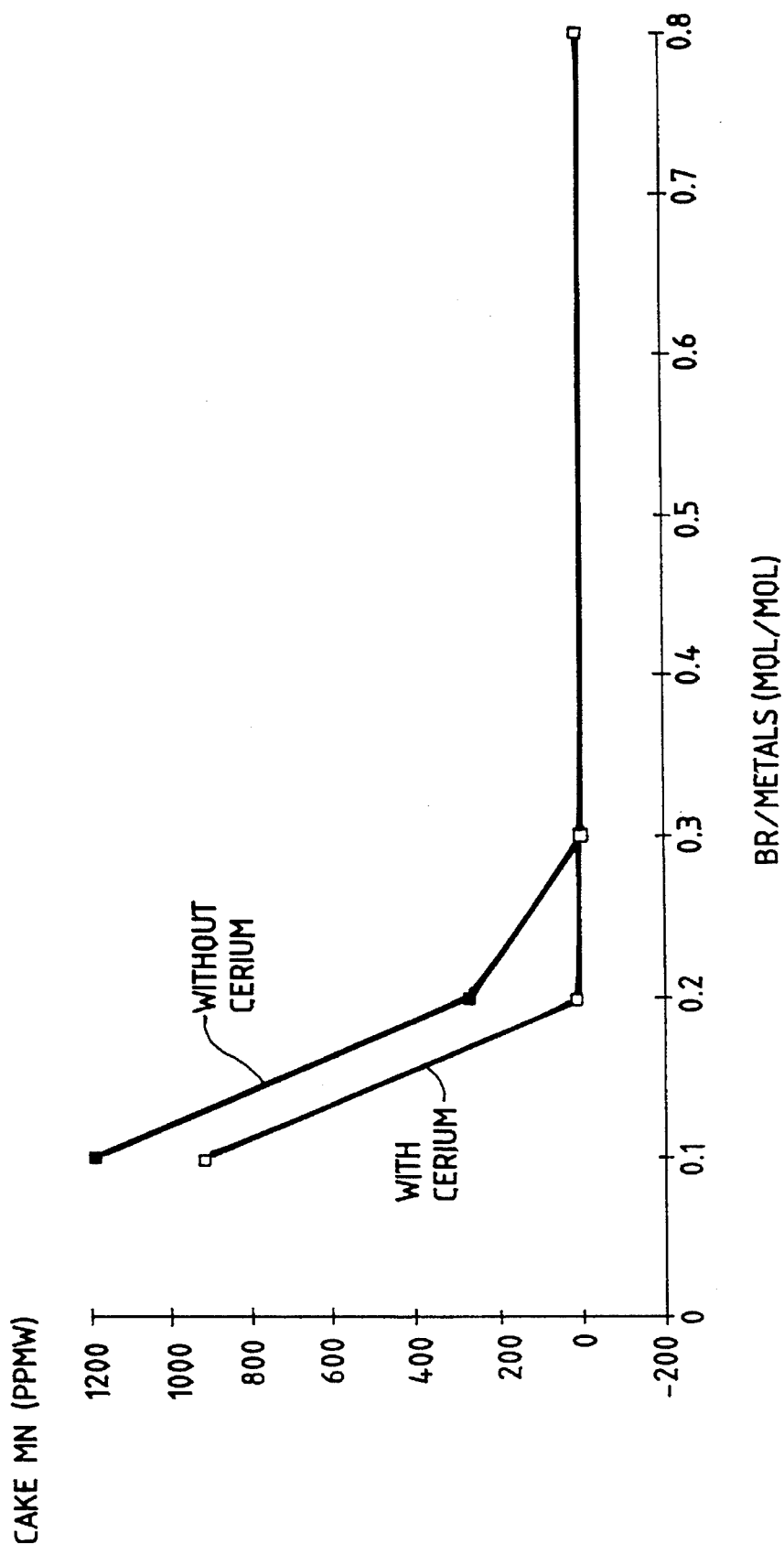
FIG. 1 demonstrates that when 0.1 mole of cerium was used in an oxidation reaction per mole of cobalt, precipitation was eliminated at a molar ratio of bromine to total of cobalt and manganese as low as 0.2. When the mole ratio of cerium to cobalt was tripled to 0.3, the molar ratio of bromine to total of cobalt and manganese could be reduced to 0.1 without precipitating manganese. It should be noted that oxidation reactions conducted at a molar ratio of bromine to total of cobalt and manganese in the range of 0.1 to 0.2 without cerium yielded a dark grey aromatic carboxylic acid product indicating the precipitation of manganese.
Figure 2:
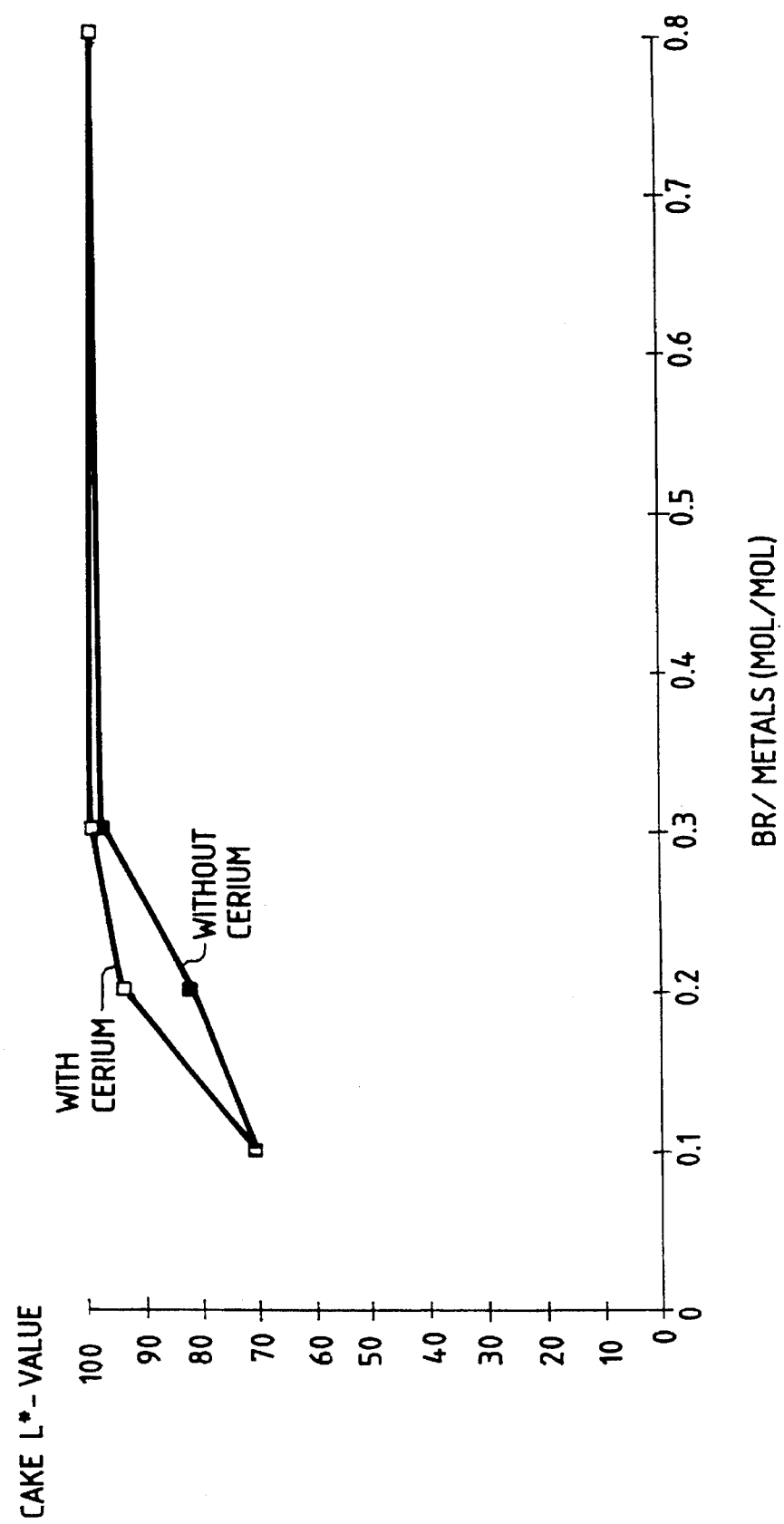

FIG. 2 illustrates that the addition of cerium to an oxidation reaction, in the ratio of about 0.1 mole cerium to 1.0 mole cobalt at a 0.2 molar ratio of bromine to total of cobalt and manganese, improved the reaction cake L* value from 82 to 94.

Figure 3:
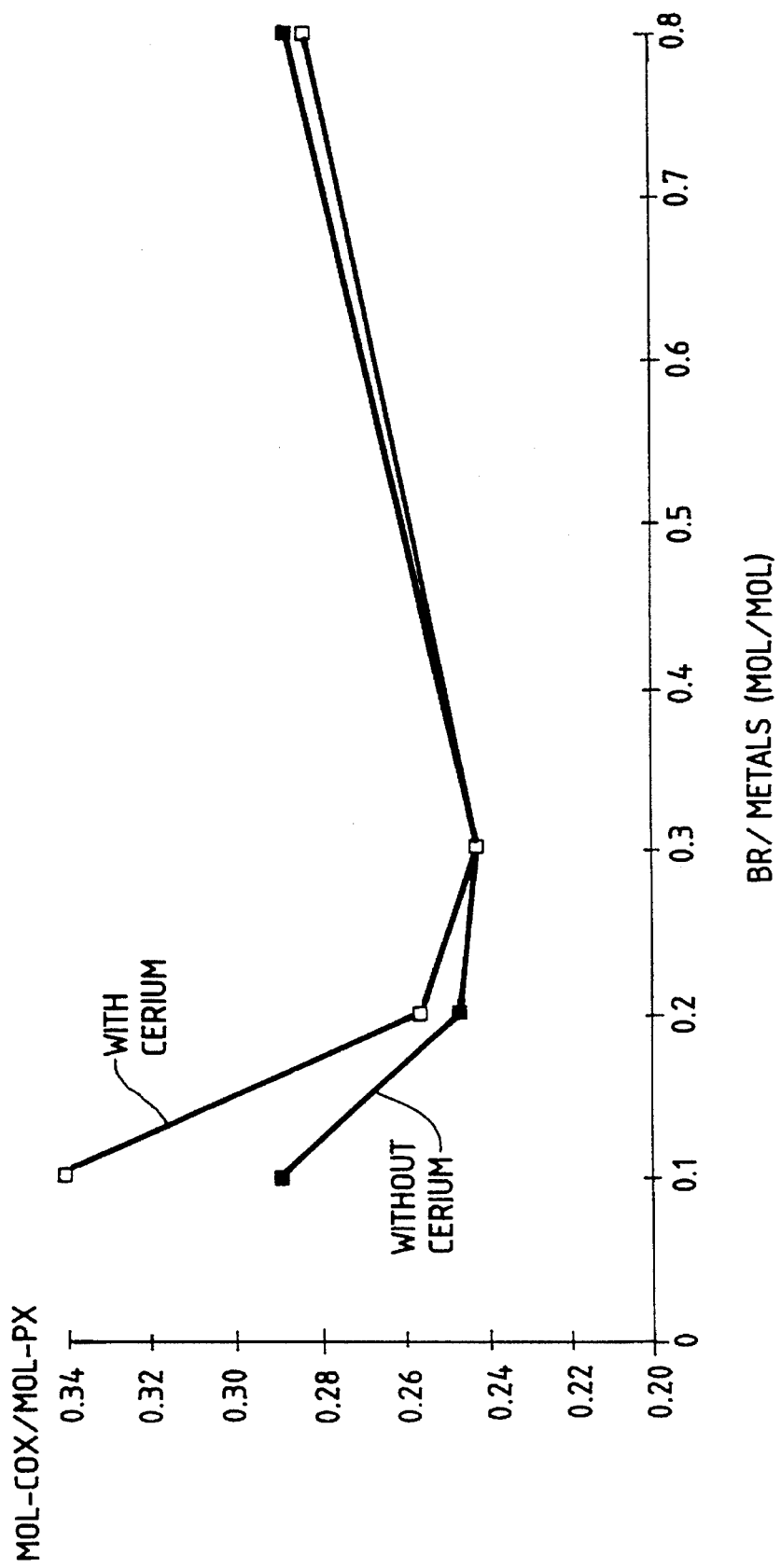

FIG. 3 illustrates that when the molar ratio of bromine in an oxidation reaction to the total of manganese and cobalt is reduced from 0.8 to about 0.2–0.3, the acetic acid and para-xylene burning is reduced by thirteen percent. This is a significant saving in operations where several hundred millions of pounds of acetic acid and para-xylene are employed. FIG. 3 illustrates that carbon oxides ($CO_x$) production was 0.287 moles of $CO_x$ per mole of para-xylene at a bromine to metals molar ratio of about 0.8, while at a 0.2–0.3 bromine to metal molar ratio, the $CO_x$ production was reduced to 0.25 mole $CO_x$ per mole of para-xylene.

Figure 4:
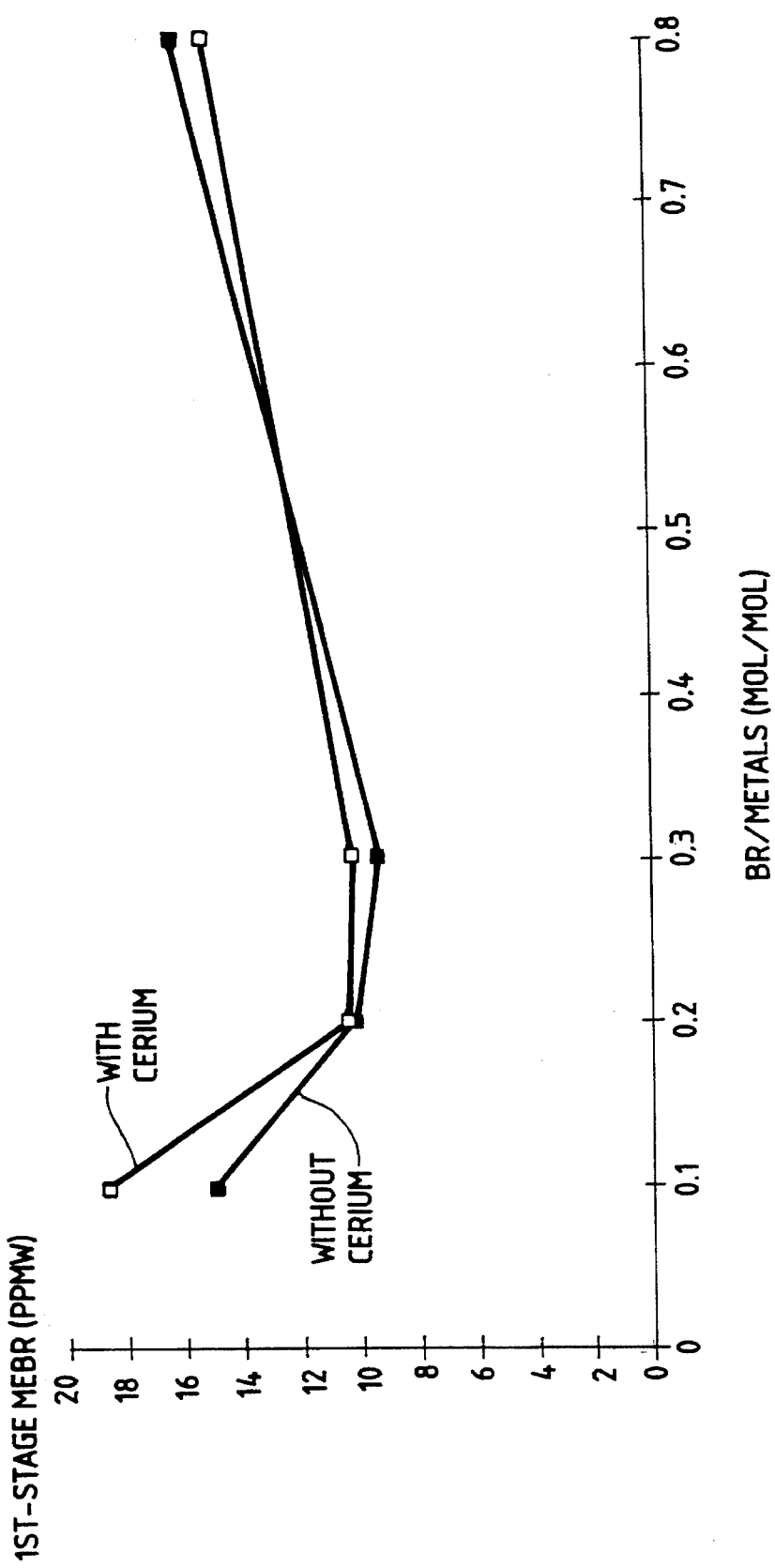

FIG. 4 illustrates that the formation of the methyl bromide was reduced about 35% by lowering the molar ratio of bromine to cobalt and manganese from 0.8 to about 0.2–0.3.

Figure 5:
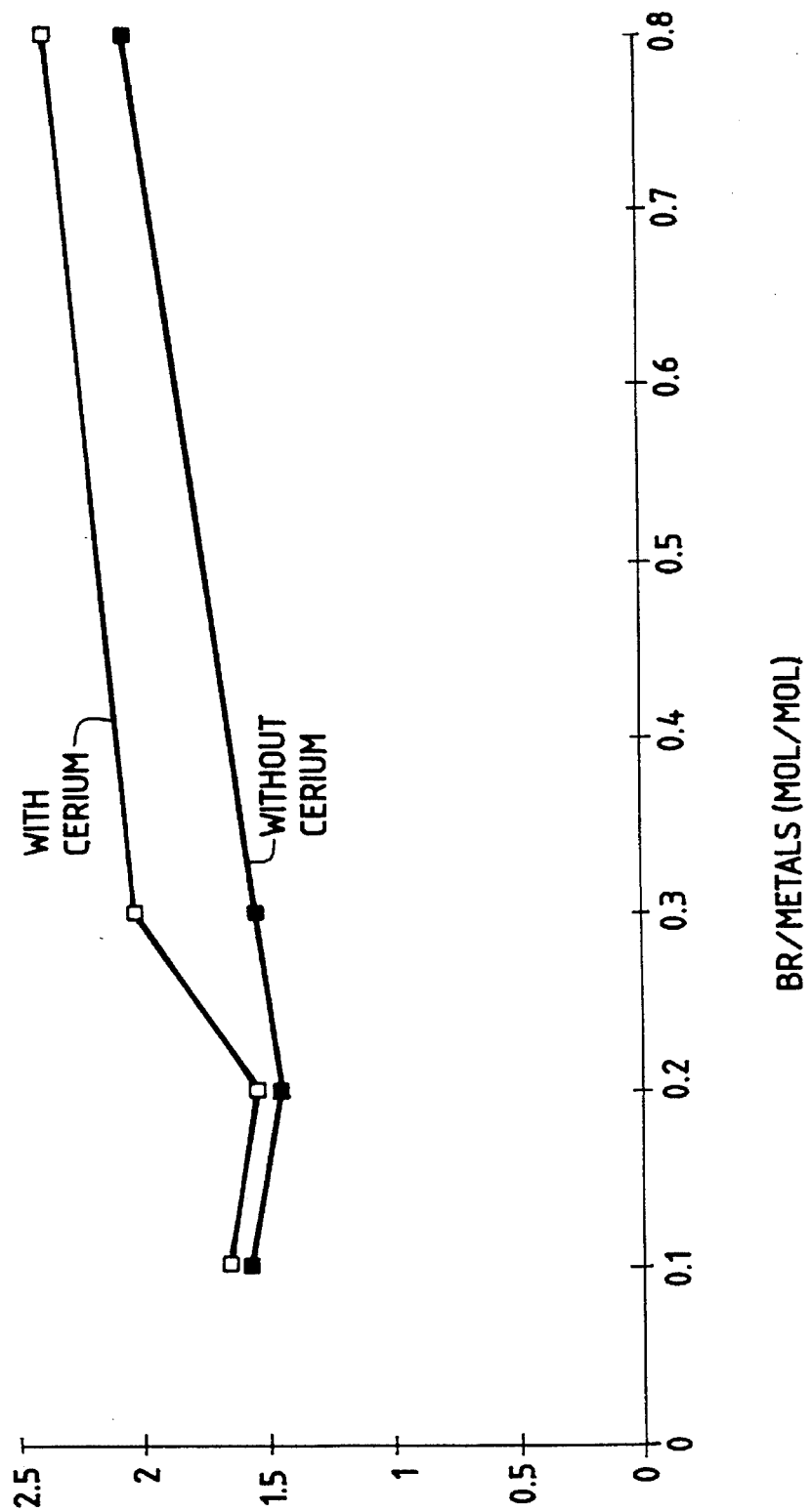

FIG. 5 illustrates that the optical properties of the terephthalic acid slurry were improved by up to 33 percent by lowering the mole ratio of bromine to total of cobalt and manganese from about 0.8 to about 0.2 in an oxidation reaction.

EXAMPLES

For the examples listed in Table 1, oxidation reactions of para-xylene to terephthalic acid were conducted in a continuous two stage titanium clad reactor. The reactions were conducted at about 180 to about 250 psig using air. The first stage reaction temperature was about 370° F. to 400° F. preferably about 370° F. to 390° F., and the second stage was conducted at a temperature of about 340° F. to about 380° F. preferably about 350° F. to 370° F. The para-xylene feed material was charged to the reactor at a rate of about 2.9 pounds per hour. The feed ratio of solvent to para-xylene was about 2.9. The solvent, acetic acid, added to the reaction contained 2.6 weight percent water.

In the first stage reactor, the vent oxygen was about three percent, and in the second step reactor, the vent oxygen was about five percent.

The data in Table 1 demonstrates that when cerium was added to the liquid phase oxidation of a dimethyl aromatic compound to an aromatic dicarboxylic acid, it was possible to use low molar ratios of bromine to total of cobalt and manganese without the precipitation of manganese. For example, a comparison of Examples 5 and 6 shows that at a molar ratio of bromine to cobalt and manganese of 0.2, manganese precipitation was abated by adding cerium.

TABLE I

Conditions and Analytical Data for Para-xylene (PX) Oxidations Conducted in the Presence of Cerium (Ce)

Oxidation Conditions[a]:

| Example No. | Feed Co (ppmw)[b] | Feed Mn (ppmw)[b] | Feed Br (ppmw)[b] | Feed (Br/Met)[c] | Feed Ce (ppmw)[b] |
|---|---|---|---|---|---|
| 1 | 227 | 380 | 718 | 0.8 | 0 |
| 2 | 227 | 380 | 718 | 0.8 | 186 |
| 3 | 344 | 576 | 400 | 0.3 | 82 |
| 4 | 344 | 576 | 400 | 0.3 | 0 |
| 5 | 434 | 782 | 338 | 0.2 | 0 |
| 6 | 434 | 782 | 388 | 0.2 | 103 |
| 7 | 781 | 1310 | 303 | 0.1 | 0 |
| 8 | 781 | 1310 | 303 | 0.1 | 185 |
| 9 | 781 | 1310 | 303 | 0.1 | 555 |

[a]First Reactor: Temperature = 386° F., Vent $O_2$ = 3%, Second Reactor: Temperature = 365° F., Vent $O_2$ = 5%.
[b]Parts per million by weight of total reactor feed.
[c]Mole ratio of bromine (Br) to total of manganese (Mn) and cobalt (Co).

Reactor Off-Gas Results:

| Example No. | Vent Gas Total $CO_x$ (mol/mol-px)[a] | Vent Gas MeBr (ppmv)[b] |
|---|---|---|
| 1 | 0.289 | 16.4 |
| 2 | 0.285 | 15.3 |
| 3 | 0.243 | 10.3 |
| 4 | 0.243 | 9.4 |
| 5 | 0.247 | 10.2 |
| 6 | 0.256 | 10.5 |
| 7 | 0.289 | 14.9 |
| 8 | 0.34 | 18.7 |
| 9 | 0.37 | 18.0 |

[a]Moles of total carbon oxides ($CO_x$) to moles of pars-xylene.
[b]Parts per million by volume by methylbromide (MeBr) in first stage Vent Gas.

Reactor Effluent Analytical Results[a]:

| Sample No. | Product Mn Concentration (ppmw) | Product Ce Concentration (ppmw) | Product OD340 | Product 4-CBA[b] Concentration | Product L* |
|---|---|---|---|---|---|
| 1 | 0 | 0 | 2.06 | 0.11 | 99 |
| 2 | 0 | 0 | 2.38 | 0.12 | 98 |
| 3 | 0 | 0 | 2.03 | 0.11 | 99 |
| 4 | 0 | 0 | 1.54 | 0.11 | 97 |
| 5 | 270 | 0 | 1.44 | 0.11 | 82 |
| 6 | <10 | 0 | 1.53 | — | 94 |
| 7 | 1190 | 0 | 1.57 | 0.12 | 71 |
| 8 | 910 | 70 | 1.65 | 0.15 | 71 |
| 9 | c | — | 1.99 | — | — |

[a]Analytical results for the terephthalic acid product from the oxidation reaction. Ce (cerium) and Mn (manganese) values are in parts per million by weight. OD340 and L* are defined above. Cerium, manganese and L* are based on isolated terephthalic acid. 4-CBA and OD340 area based on the reaction slurry.
[b]4-carboxybenzaldehyde in parts per million by weight.
[c]No visible evidence of any manganese precipitation.

The experiments recorded in Tables II and III illustrate the effect of cerium in reducing or eliminating manganese precipitation.

The experiments set forth in Tables II and III are based on the principle that 4-carboxybenzaldehyde (4-CBA) oxidizes in the cobalt-manganese-bromine catalyst system by formation of a 4-carboxyperbenzoic acid and then further to terephthalic acid. A readily available peracid which is similar to 4-carboxyperbenzoic acid is 3-chloroperbenzoic acid (MCPBA). MCPBA in the presence of mixtures of the cobalt-manganese-bromine catalyst system is known to undergo a series of reactions as follows, where only the oxidation states of the metals are indicated:

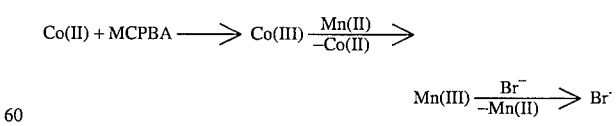

In the absence of bromide and with the requisite temperature, concentration and amount of water, we discovered that some of the Mn(III) disproportionates to Mn(IV) and then precipitates out as manganese (IV) oxide as follows:

Although not intending to be bound by a theory of operation, we believe that our invention eliminates such reaction. The precipitation effect, as shown in Table III, can be obtained in laboratory reactions by mixing together MCPBA, cobalt acetate and manganese acetate.

In liquid phase oxidation experiments it was discovered that terephthalic acid solids turn grey when the water concentration in the reaction increases. This effect is also repeated in the examples set forth in Table III. The acetic acid solution formed by mixing a solution of MCPBA with a cobalt-manganese mixture remains clear at 0 percent and twenty percent water, but a fine black precipitate formed at about twenty five percent to about forty percent water. This is shown in Tables II and III runs A and B, and C–F. When the bromine to cobalt, manganese concentration is increased, the precipitation is abated. See examples G-I Tables II and III.

When cerium (III) acetate was added to the bromine-cobalt-manganese system discussed above, the solution remained clear after the MCPBA was added and no manganese dioxide precipitate formed. The manganese dioxide precipitation was avoided at cerium to cobalt plus manganese molar ratios as low as 0.0312. See Table II Examples J and K, L–U, and W and X.

We conducted comparative examples with nickel (II) acetate (see example A1 in Tables II and III) and chromium (III) acetate hydroxide (see examples Y and D-1 in Tables II and III). When nickel was substituted for cerium, a dark manganese dioxide precipitate formed. When chromium was substituted for cerium, a pink precipitate formed. This was identified as an impurity comprising about 36 percent cobalt (II) acetate. The precipitation of cobalt acetate is unacceptable since it is the expensive part of the catalyst package. It also would contaminate the aromatic carboxylic acid product cake. Iron also prevents the precipitation of the manganese dioxide, but iron cannot be used in bromine-cobalt-manganese catalyzed oxidations because it tends to deactivate the hydrogenation catalyst used in the subsequent purification step.

TABLE II

Experiments for Manganese (IV) Precipitation[a]

| Sample No. | Additive | Additive/ metals, mol/mol | % (vol.) $H_2O$ | Visual Result |
|---|---|---|---|---|
| A | None | | 0 | clear solution |
| B | None | | 20 | clear solution |
| C | None | | 25 | dark ppt forms |
| D | None | | 30 | dark ppt forms |
| E | None | | 35 | dark ppt forms |
| F | None | | 40 | dark ppt forms |
| G | NaBr | 0.5 | 25 | dark ppt forms |
| H | NaBr | 1.0 | 25 | amber to cranberry |
| I | NaBr | 2.0 | 25 | amber, then purple |
| J | Ce(III) acetate | 1.8 | 25 | clear |
| K | Ce(III) acetate | 0.92 | 25 | clear |
| L | Ce(III) acetate | 2.0 | 25 | clear amber |
| M | Ce(III) acetate | 1.0 | 25 | clear amber |
| N | Ce(III) acetate | 0.5 | 25 | clear amber |
| O | Ce(III) acetate | 0.25 | 25 | clear amber |
| P | Ce(III) acetate | 0.125 | 25 | clear amber |
| Q | Ce(III) acetate | 0.0625 | 25 | clear amber |
| R | Ce(III) acetate | 0.125 | 25 | clear amber |
| S | Ce(III) acetate | 0.0625 | 25 | clear amber |
| T | Ce(III) acetate | 0.25 | 25 | clear amber |
| U | Ce(III) acetate | 0.0312 | 25 | clear amber |
| V | None | | 25 | dark ppt forms |
| W | Ce(III) acetate | 1.0 | 25 | clear |
| X | Ce(III) acetate | 0.5 | 25 | clear |
| Y | Cr(III) acetate hydroxide | 1.0 | 25 | pink ppt forms |
| Z | Fe(II) acetate | 1.0 | 25 | clear, amber |
| A1 | Ni(II) acetate | 1.0 | 25 | dark ppt forms |
| B1 | None | | 25 | dark ppt forms |
| C1 | Ce(III) acetate | 0.10 | 25 | clear, no solids |
| D1 | Cr(III) OAc hydroxide | 0.10 | 25 | pink ppt forms |
| E1 | Fe(III) acetate | 0.10 | 25 | white solids |
| F1 | FE(III) Cl$_3$ | 0.10 | 25 | white solids |

[a]Initial concentration of cobalt (II) and manganese (II) acetates (metals) were 0.0100M in acetic acid. Sufficient MCPBA added to oxidize 50% of the manganese to Mn(III). The MCPBA was added to a boiling solution of the cobalt (II) and manganese (II) acetates. It was then boiled for an additional 15 min., then cooled to room temperature overnight. The visual given in this table were made after cooling to room temperature. The solids were then filtered through a millipore filter the next morning. In this Table and Table III, "ppt" means precipitate.

TABLE III

XRF Data on Filtrates from Manganese Precipitation Experiments[a]

| Sample | $H_2O$, % | ppt. g[b] | Filtrate[c] weight, g | Co, ppm | Mn, ppm | Mn/Co mol/mol |
|---|---|---|---|---|---|---|
| A | 0 | None | 108.06 | 549 | 553 | 1.080 |
| B | 20 | None | 119.42 | 490 | 500 | 1.094 |
| C | 25 | 0.0020 | 84.13 | 612 | 541 | 0.948 |
| D | 30 | 0.0050 | 93.71 | 608 | 550 | 0.970 |
| E | 35 | 0.0120 | 91.43 | 587 | 479 | 0.875 |
| F | 40 | 0.0170 | 91.97 | 593 | 465 | 0.841 |
| I | 25 | None | 90.89 | 614 | 581 | 1.023 |
| H | 25 | None | 105.93 | 532 | 505 | 1.027 |
| G | 25 | 0.0060 | 106.60 | 533 | 485 | 0.984 |
| V | 25 | 0.0020 | 96.25 | 840 | 730 | 0.932 |
| W | 25 | 0.0000 | 97.38 | 730 | 650 | 0.955 |
| X | 25 | 0.0000 | 99.14 | 940 | 800 | 0.912 |
| Y[d] | 25 | 0.0044 | 82.76 | 580 | 780 | 1.442 |
| A | 25 | 0.0000 | 97.26 | 810 | 730 | 0.966 |
| A1 | 25 | 0.0887 | 94.87 | 960 | 800 | 0.893 |
| B1 | 25 | 0.0023 | 99.16 | 590 | 510 | 0.927 |
| C1 | 25 | 0.0000 | 97.26 | 590 | 540 | 0.981 |
| D1 | 25 | 0.0051 | 74.36 | 570 | 520 | 0.978 |
| E1 | 25 | 0.0007 | 94.10 | 710 | 630 | 0.951 |
| F1 | 25 | 0.0010 | 96.25 | 660 | 580 | 0.942 |

[a]X-ray florescence analysis (XRF) data
[b]Weight of recovered precipitate in grams.
[c]Analysis of filtrate, i.e. reaction mixture after separation from precipitate. Total weight of filtrate given in grams. Cobalt (Co), Manganese (Mn) values are parts per million by weight of filtrate.
[d]A given weight of the pink solids were dissolved in water and analyzed for cobalt and manganese. Solids accounted for 34.6% cobalt in Y and 1.9% cobalt in D1.

Cerium has a positive effect on the preparation of polyester materials made from aromatic dicarboxylic acids. When terephthalic acid, for example, was condensed with ethylene glycol to prepare polyethyleneterephthalate (PET), the presence of cerium in the polymerization reaction at levels of 25 to 50 parts per million by weight, for example, accelerated the polymerization reaction. Thus, a mixture of ethylene glycol and terephthalic acid in a mole ratio of about 1.2, respectively, was reacted at a temperature of about 260° C., under nitrogen gas, at a pressure of about 50 psig, to form a prepolymer. Increasing the temperature to about 285° C., reducing the pressure to about 1 mm/Hg, and simultaneously removing excess ethylene glycol resulted in the polymerization of the prepolymer to form PET. The inclusion of cerium in the form of cerium (III) acetate, for example, either before or after the formation of prepolymer resulted in a faster polymerization reaction.

While only certain embodiments of the present invention have been set forth, alternative embodiments and various modifications will be apparent from the above description to those skilled in the art. These alternatives are considered equivalent and within the spirit and scope of the present invention.

Having described the invention, that which is claimed is:

1. A process for oxidation of a dimethyl benzene aromatic compound with molecular oxygen to the corresponding aromatic dicarboxylic acid at elevated temperature and under liquid phase conditions in the presence of a metal catalyst comprising cobalt, manganese and cerium components, a source of bromine, and a C1–C6 aliphatic carboxylic acid solvent, and at low molar ratios of bromine to the total of cobalt and manganese thereby reducing corrosion and the formation of methyl bromide, which process comprises conducting the oxidation in an oxidation reaction mixture wherein the mole ratio of cerium to cobalt is about 0.005 to about 1.0, and the mole ratio of bromine to the total of cobalt and manganese is about 0.1 to less than about 0.5, and wherein the cerium functions to prevent the precipitation of manganese.

2. The process of claim 1 wherein para-xylene is oxidized to terephthalic acid.

3. The process of claim 1 wherein ortho-xylene is oxidized to ophthalic acid.

4. The process of claim 1 wherein meta-xylene is oxidized to isophthalic acid.

5. The process of claim 1 wherein cobalt is present in the oxidating reaction mixture at a level of about 40 to about 5000 parts per million by weight.

6. A process for oxidation of para-xylene with molecular oxygen to terephthalic acid at elevated temperatures and under liquid phase conditions in the presence of acetic acid solvent, a bromine component, and a metal catalyst comprising cobalt, manganese and cerium components, a source of bromine and at low molar ratios of bromine to the total of cobalt and manganese thereby reducing corrosion and the formation of methyl bromide, which process comprises conducting the oxidation in an oxidation reaction mixture wherein the mole ratio of cerium to cobalt is about 0.005 to about 1.0, the mole ratio of bromine to the total of cobalt and manganese is about 0.1 to less than about 0.5, and wherein the cerium function to prevent the precipitation of manganese.

7. The process of claim 6 wherein the mole ratio of cerium to cobalt is about 0.01 to about 0.3.

8. The process of claim 6 wherein the molar ratio of bromine to cobalt and manganese is about 0.1 to about 0.45.

9. A continuous process for oxidizing para-xylene with molecular oxygen to terephthalic acid under liquid phase conditions in the presence of acetic acid solvent wherein a first stage oxidation is conducted at a temperature of about 370° F. to about 400° F. and the second stage is conducted at a temperature of about 340° F. to about 380° F. in the presence of cerium at a low molar ratio of bromine to total of cobalt and manganese thus reducing corrosion and methyl bromide formation, which process comprises conducting such oxidation in the presence of a catalyst system comprising a source of bromine and metal components comprising manganese, cobalt and cerium wherein the mole ratio of cerium to cobalt is in the range of about 0.005 to about 1.0 and the molar ratio of bromine to total cobalt and manganese is in the range of about 0.1 to about 0.45, and wherein cerium functions to prevent the precipitation of manganese from the reaction mixture.

10. The process of claim 9 wherein the mole ratio of cerium to cobalt is about 0.01 to about 0.3.

11. The process of claim 9 wherein the molar ratio of bromine to total of cobalt and manganese is about 0.125 to about 0.40.

12. The process of claim 9 wherein the first stage oxidation is conducted at a temperature of about 370° to about 390° F. and the second stage oxidation is conducted at a temperature of about 340° to about 370° F.

13. The process of claim 1 wherein the aromatic dicarboxylic produced thereby is purified by treating the aromatic dicarboxylic acid with hydrogen gas in the presence of a hydrogenation catalyst.

14. The process of claim 1 wherein the molar ratio of cerium to cobalt is about 0.01 to about 0.3 and the molar ratio of bromine to total of cobalt and manganese is about 0.1 to about 0.3.

* * * * *

UNITED STATES PATENT AND TRADEMARK OFFICE
CERTIFICATE OF CORRECTION

PATENT NO. : 5,453,538

DATED : September 26, 1995

INVENTOR(S) : Jeffrey L. Broeker, Walter Partenheimer, Bruce I. Rosen

It is certified that error appears in the above-indentified patent and that said Letters Patent is hereby corrected as shown below:

| Col. | Line | |
|---|---|---|
| 7 | 35 | in "TABLE I" in the footnote labeled "a" underneath the section titled "Reactor Off-Gas Results:" patent reads "aMoles of total carbon oxides ($CO_x$) to moles of pars-xylene." patent should read --aMoles of total carbon oxides ($CO_x$) to moles of para-xylene.-- |
| 10 | 20 | in the footnote "a" under "TABLE II-continued" patent reads "The visual given in this table" patent should read --The visual result given in this table-- |

Signed and Sealed this

Thirteenth Day of February, 1996

Attest:

BRUCE LEHMAN

Attesting Officer   Commissioner of Patents and Trademarks